United States Patent [19]

Cosentino et al.

[11] 4,021,341
[45] May 3, 1977

[54] HERMODIALYSIS ULTRAFILTRATION SYSTEM

[76] Inventors: Louis C. Cosentino, 2435 Holly Lane North, Wayzata, Minn. 55391; B. Steven Springrose, 3510 Lyndale North, Minneapolis, Minn. 55412

[22] Filed: Oct. 15, 1975

[21] Appl. No.: 622,755

Related U.S. Application Data

[63] Continuation of Ser. No. 443,700, Feb. 19, 1974, abandoned.

[52] U.S. Cl. .............................. 210/87; 210/103; 210/321 B
[51] Int. Cl.² .................. B01D 31/00; B01D 13/00
[58] Field of Search ............... 210/22, 23, 97, 103, 210/138, 321, 416, 87

[56] References Cited

UNITED STATES PATENTS

| | | | |
|---|---|---|---|
| 3,669,880 | 6/1972 | Marantz et al. | 210/22 |
| 3,844,940 | 10/1974 | Kopf et al. | 210/22 |
| 3,939,069 | 2/1976 | Granger et al. | 210/22 A |

*Primary Examiner*—Frank A. Spear, Jr.
*Attorney, Agent, or Firm*—Schroeder, Siegfried, Ryan & Vidas

[57] ABSTRACT

An improved hemodialysis ultrafiltration system. Dialysate input and output pumps are linked to maintain their volume flows substantially equal. A pressure attenuator and a pressure amplifier on the dialyzer dialysate inlet and outlet, respectively, are employed to control dialyzer pressure on the dialysate side. Dialysate output in excess of dialysate input is separated through the action of the dialysate output pump for measurement. The ultrafiltration rate may be controlled through the pressure transformers and the instantaneous ultrafiltration rate and total ultrafiltration volume may be continuously monitored.

17 Claims, 2 Drawing Figures

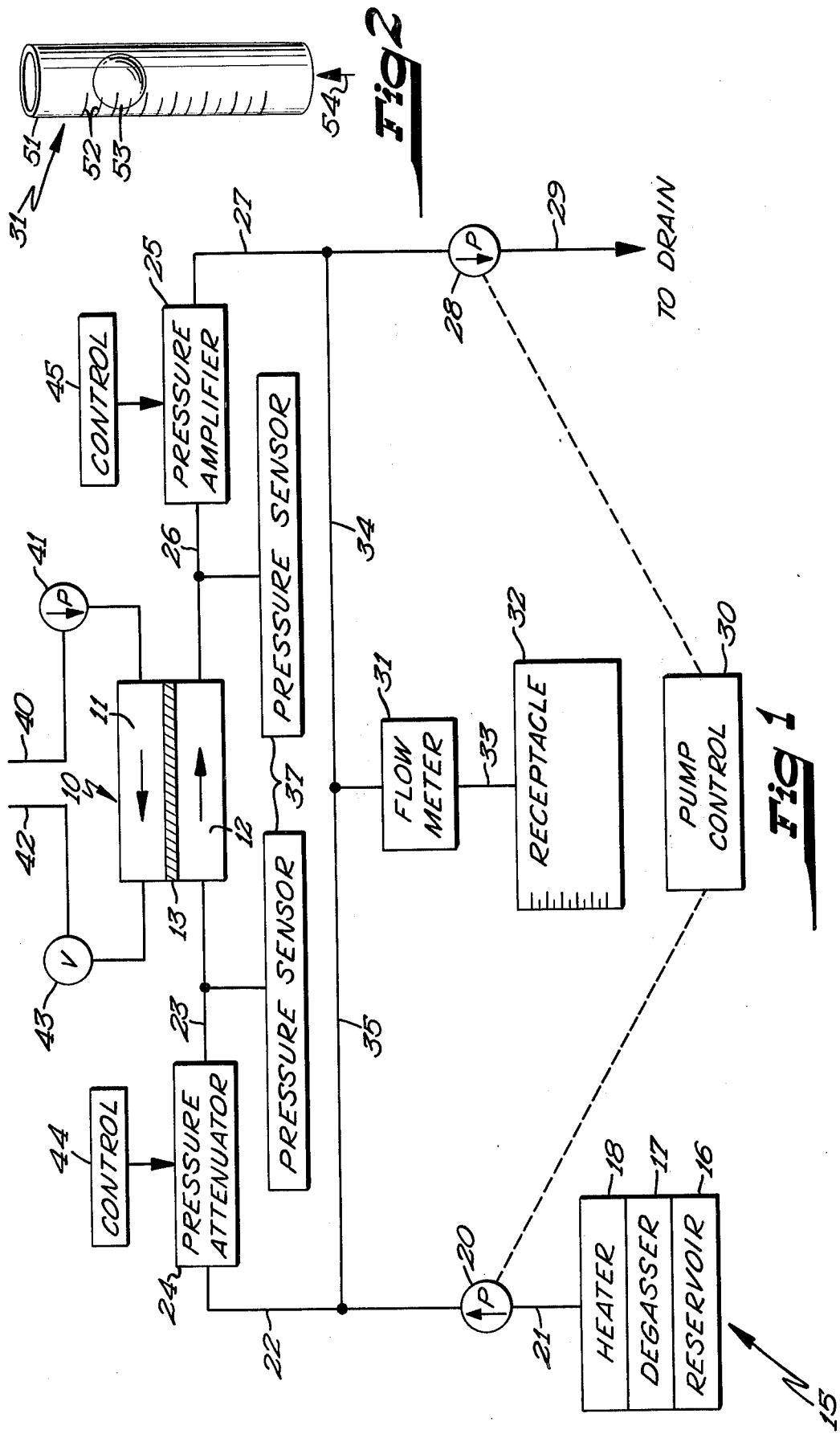

HERMODIALYSIS ULTRAFILTRATION SYSTEM

This is a Continuation of application Ser. No. 443,700, filed Feb. 19, 1974, now abandoned.

BACKGROUND OF THE INVENTION

Dialysis of te blood or hemodialysis is a well known and accepted medical technique. For example, kidney malfunction or failure requires that kidney function be performed artificially, as through hemodialysis.

Successful hemodialysis involves the removal of waste materials and excess water. The removal of waste materials is effectively accomplished through prior art hemodialysis systems which may also compensate, through replacement, for the removal of too much of a particular blood consitituent, glucose, for example. The controlled removal of excess water, on the other hand, has proven to be major problem in hemodialysis. Excess water is removed by unltrafiltration which is established by maintaining the dialysate pressure within the dialyzer lower than that of the blood pressure. Prior art hemodialysis systems have established this pressure condition and monitored it through the use of pressure gauges on the dialysate side. However, these prior art systems have been unable to even estimate the ultrafiltration rate with any accuracy.

The removal of too much water too fast will cause a hemodialysis patient to go into shock. Because the ultrafiltration rate cannot accurately be determined for prior art hemodialysis systems, those systems have been operated at very low ultrafiltration rates. This has been one factor underlying the extremely long time of dialysis.

One solution to the above mentioned difficulty in establishing ultrafiltration rate with prior art hemodialysis systems has been to place the dialysis patient on a weighing bed to determine the amount of water removal by the decrease in patient weight. Obviously, this system has an extremely high cost and is available only in those situations where some control over, or a knowledge of, the ultrafiltration volume is absolutely necessary. Also, the weighing bed technique will not indicate the instantaneous ultrafiltration rate.

SUMMARY OF THE INVENTION

The present invention provides a new dialysate circuit for a hemodialysis system which makes it possible to control the ultrafiltration rate as well as providing continuously monitoring means for the instantaneous ultrafiltration rate and total ultrafiltration volume. This is accomplished through dialysate input and output pumps and a pressure attenuator and a pressure amplifier on the dialyzer dialysate inlet and outlet, respectively. The pressure attenuator and pressure amplifier control dialyzer pressure on the dialysate side and, thus, the ultrafiltration rate.

The amount by which the dialysate output exceeds the dialysate input is the ultrafiltrate volume. That is, the excess is the contribution to the total dialysate volume flow attributable to ultrafiltration. The excess is separated from the total dialysate output volume flow by the removal of an amount of dialysate equivalent to the dialysate input volume flow. This is accomplished through the input and output dialysate pumps which are linked to maintain their volume flow substantially equal. That portion of the dialysate output volume flow attributable to ultrafiltration may be measured instantaneously, as by a flow meter, or the total ultrafiltration volume may be measured as in a graduated receptacle, or both. With a knowledge of the instantaneous ultrafiltration rate and/or the total ultrafiltration volume, it is possible to make a meaningful adjustment in the ultrafiltration rate by changing the dialyzer dialysate pressure thereby providing an effective control for the ultrafiltration rate itself.

The many objects, advantages and novel features of the present invention will become apparent from the following detailed description when considered in conjunction with the accompanying drawings.

BRIEF DESCRIPTION OF THE DRAWINGS

FIG. 1 is a diagrammatical illustration of the present invention.

FIG. 2 illustrates a preferred embodiment of the flow meter in the embodiment of FIG. 1.

DETAILED DESCRIPTION OF THE DRAWINGS

FIG. 1, which illustrates a preferred embodiment of the present invention, shows a dialyzer 10 having a blood side 11 and a dialysate side 12 separated by a membrane 13. The dialyzer 10 may be any of those known to the prior art with regard to the configuration of membrane 13. That is, dialyzer 10 may be of the type wherein the membrane 13 is in the form of a flat sheet or, alternatively, the membrane 13 may be tubular or any other configuration. In the tubular configuration known to the prior art, the blood flows within the tubular members formed by the membrane while the dialysate flows along the outer wall of the tubes. The selection of membrane material is known to the prior art and is dependent primarily upon the waste materials to be removed from the blood. With all such membranes, ultrafiltration may be obtained through the maintenance of proper pressure gradients across the membrane.

A dialysate source is illustrated at 15 in FIG. 1 and is comprised of a dialysate reservoir 16, a dialysate degasser 17 and a dialysate heater 18. The utility of the degasser 17 and heater 18 in a hemodialysis system is well known to the prior art as are the particular configurations of all the elements combining to form an appropriate source of dialysate. Of course, the present system is not limited to the use of a reservoir 16, degasser 17 and heater 18 but may be employed with any dialysate makeup system known to the prior art.

Dialysate from the source 15 is passed to a pump 20 via a line 21. The exhuast of the pump 20 is connected to a pressure attenuator 24 via a line 22 and a line 23 connects the pressure attenuator 24 to the input of the dialysate side 12 of the dialyzer 10. The output of the dialysate side 12 of the dialyzer 10 is connected to a pressure amplifier 25 via a line 26. A line 27 connects the pressure amplifier 25 to the inlet of a pump 28 whose exhaust is connected to a drain by a line 29.

The pumps 20 and 28 are linked as at 30 to maintain their volume flow substantially equal. The link 30 may take the form of a mechanical linkage or any other control which will satisfy the stated condition of substantial equivalence in volume flow. Preferably, pumps 20 and 28 are positive displacement or constant volume pumps operated at or near zero pressure drop. As is known to the prior art, this type of pump, when operated at the stated pressure condition, has a substantially constant volume flow. Also, to facilitate maintaining their volume flow substantially equal, the pumps 20 and 28 may be identical.

A flow meter 31 is connected to a receptacle 32 via a line 33 and both are connected to the line 27 by a line 34. A line 35 interconnects the line 22 and the line 34. Pressure sensors 37 are connected into the lines 23 and 26.

The dialyzer blood circuit consists essentially of a line 40 having a pump 41 connected into the blood inlet of the dialyzer 10 and a line 42 having a valve 43 connected into the blood outlet of the dialyzer 10. The lines 40 and 42 are suitably connected to the patient who is to undergo hemodialysis in known manner. The pressure in the blood side 11 of the dialyzer 10 is controlled through the action of the pump 41 in conjunction with the valve 43. A blood circuit may be as shown in FIG. 1 or, alternatively, may be any other suitable configuration known to the prior art.

The pressure attenuator 24 is a pressure drop device which acts to maintain the pressure in line 23 below the pressure in line 22. The pressure amplifier 25 is a pressure rise device which acts to maintain the pressure in line 27 above the pressure in line 26. Thus, the pressure attenuator 24 and pressure amplifier 25 work in conjunction to control the pressure in the dialysate side 12 of the dialyzer 10. Pressure attenuator 24 and pressure amplifier 25 may be controlled, in known manner, through suitable cooperating controls 44 and 45 respectively.

To maintain the pressure of dialysate side 12 below that of blood side 11 and establish ultrafiltration, it is usually necessary that the pressure of the dialysate side be negative which requires that the pressure amplifier 25 be active. That is, te conditions to establish ultrafiltration usually require that pressure amplifier 25 be a pump and preferably a variable output pump whose output may be controlled in known manner as by control 45. The pressure attenuator 24, on the other hand, need only create pressure drop. Thus, pressure attenuator 24 may be either a valve or a pump, the volume flow and/or pressure drop of either being controlled in know manner as by control 44. When the pressure attenuator 24 and/or pressure amplifier 25 are pumps, it is preferred that they be positive displacement pumps with control 44 establishing the volume flow of pressure attenuator-pump 24 approximately equal to the volume flow of pump 20 and control 45 establishing the volume flow of pressure amplifier-pump 25 to be approximately equal to the volume flow of pump 20 plus the ultrafiltrate volume flow.

In operation, and assuming that pressure attenuator 24 is a valve having a volume flow rate approximately equal to the volume flow rate at the pump 20, the pump 20 will draw dialysate from the source 15 and pump it at a preset and relatively constant volume flow over the line 22 to the pressure attenuator 24. The pressure attenuator 24, in conjunction with the pressure amplifier 25, will maintain the pressure in the dialysate side 12 of the dialyzer 10 below that of the blood side 11. Of course, on start up it may be necessary to regulate the pressure drop across pressure attenuator 24 and pressure rise across pressure amplifier 25 to obtain the initial operating conditions. With the dialysate side pressure in proper relation to the blood side pressure, ultrafiltration will occur and the volume flow of dialysate out of the dialyzer 10 will be greater than the input volume flow by an amount substantially equal to the amount of ultrafiltrate. The difference in dialysate inlet and outlet volume flows is referred to herein as the ultrafiltrate volume. The total volume flow out of the dialyzer dialysate side 12 will be transmitted to pressure amplifier 25 by a line 26 and, from there, into line 27. Pump 28, its volume flow being previously set to be substantially equal to that of pump 20, will withdraw dialysate from the line 27 at a rate substantially equal to the rate with which dialysate is put into the system by pump 20. The amount not withdrawn from line 27 is the ultrafiltrate volume which is transmitted by a line 34 to a flow meter 31 where an instantaneous ultrafiltration rate may be established and ultimately to a receptacle 32. The receptacle 32 may be of the type having a known volume with predetermined volume markings on its side wall, as at 50, such that a total amount of water removed by ultrafiltration may be determined at any time and the ultrafiltration rate for the entire period of hemodialysis may be continuously monitored. It should be noted that the ultrafiltrate volume is not the ultrafiltrate but, an amount of dialysate and ultrafiltrate equal to the amount of ultrafiltrate.

With a precise matching of the volume flow of pressure attenuator 24 and pump 20, there will be no flow in line 35. As an alternative to precisely matching the volume flow of the pressure attenuator 24 to that of the pump 20, and particularly when the pressure attenuator 24 is a pump, it is necessary to provide some means of compensation for any difference in volume flow. This compensation is accomplished through the line 35. When operating with a pump as pressure attenuator 24, the pump 20 will again withdraw a preset amount of dialysate from the dialysate source 15. The pressure attenuator 24 and pressure amplifier 25 (both pumps in this embodiment) will operate as described above to maintain a pressure in the dialysate side below that of the blood side of the dialyzer 10. Again, the pump 28 will withdraw from the line 27 an amount of dialysate equivalent to that put into the system by the pump 20. If there is a difference in volume flow between the pump 20 and pump 34, there will be a dialysate flow established in the line 35. That is, if the pump 20 has a volume flow greater than that of the pump 24, a dialysate flow in the line 35 will be established to the flow meter 31. On the other hand, if the pump 24 has a greater volume flow than that of the pump 20 a dialysate flow through the line 35 to the pump 24 will be established. In either case, the volume flow of the pressure attenuator-pump 24 will establish the actual dialysate input into the dialyzer 10.

Since the amount of the dialysate withdrawn from line 27 by the pump 28 is matched to that of the input to line 22 of the pump 20, the amount withdrawn from the line 27 may not precisely correspond to the actual dialysate input via the pressure attenuator-pump 24. However, any dialysate flow in the line 35 will be summed with the dialysate flow in the line 34 to give a precise measurement of ultrafiltration rate. For example, if the pressure attenuator-pump 24 has a volume flow less than that of pump 20 (and thus pump 28) the amount withdrawn by the pump 28 will exceed the actual dialysate input. The amount by which the amount withdrawn by pump 28 exceeds actual dialysate input will correspond to the amount flowing in the line 35. Thus, when the amount of dialysate flowing in the line 35 is summed with the volume flow in line 34 and metered at 31, the ultrafiltration rate measurement will be accurate. Conversely, if the volume flow of pressure attenuator-pump 24 exceeds that of pump 20 the amount of dialysate input into the dialyzer will be in excess of that withdrawn by a pump 28. However, this excess will be withdrawn from the line 34 over the line 35 and thus will not be measured in the flow meter 31. It should be noted that the preferable, but not critical, condition is to have the line 35 carrying a flow from the pump 20 to the flow meter 31 in either the valve or pump mode of pressure attenuator 24. This eliminates the need for precisely matching the volume flow of pump 20 and pressure attenuator 24 while assuring that once circulated dialysate is not recirculated.

From the above, it is apparent that the present invention provides a novel ultrafiltration system having the capability to measure the ultrafiltration rate during hemodialysis. Since an accurate measurement of ultrafiltration rate is possible, it is also possible to precisely control the ultrafiltration rate. For example, if the ultrafiltration is too low the dialysate side pressure may be reduced by operating on either or both of the pressure attenuator 24 and pressure amplifier 25 through their respective controls 44 and 45. Conversely, if the ultrafiltration rate is too high for patient safety the dialysate side pressure may be increased — while maintaining it below a blood side pressure — by operation upon the pressure attenuator 24 and/or pressure amplifier 25 through their respective controls 44 and 45. While both modes discussed herein (valve and pump as pressure attenuator 24) provide ultrafiltration rate measurement and control not heretofore available in any prior art system it has been found advantageous to operate in the pump mode. This results from the fact that a pump operating as attenuator 24 will automatically adjust to changes in output pressure to maintain the transmembrane pressure and, thus, the ultrafiltration rate relatively constant. Such pressure changes and their causes are known to the prior art. Also, with a dual pump operation it is possible to reverse the transmembrane pressure gradient to accomplish "reverse" ultrafiltration (i.e. from dialysate to blood).

The pressure sensors 37 are tapped into either or both of the lines 23 and 26 to give an indication of the dialysate side pressure. The controls 44 and 45 are adjusted to control dialysate side pressure in accordance with the measurement of ultrafiltration rate and the dialysate side pressure may be read with appropriate pressure sensors 37. Also, if the dialysate side pressure gets too negative, there is the danger that the membrane 13 will rupture. The pressure sensors 37 may be employed to sound an alarm or otherwise give an indication of unsafe pressure on the dialysate side 12 or shut down the system.

Referring now to FIG. 2 there is shown a flow meter 31 suitable for use within the embodiment of FIG. 1. The flow meter 31 is of the type commonly referred to as a ball type flow meter having a transparent vertical tubular member 51 with flow rate markings 52 marked on the side wall. A ball 50 having a mass selected for the particular fluid to be measured is positioned within the member 51 and a flow of fluid whose flow rate is to be determined is introduced into the member 51 in the direction indicated by the arrow 54. Gravity will act upon the ball 53 tending to bring it to the bottom of the tube while the force exerted on the ball 53 by the flow through the member 51 will tend to raise the ball 53. Assuming a constant flow rate, these two forces acting on the ball will cause the ball to establish a vertical equilibrium position within the member 51 corresponding to the flow rate. At lower flow rates, the ball will assume a lower position while higher flow rates will cause the ball to rise within the member 51. Ball type flow meters of the type illustrated are well known in the art and their calibration is within the knowledge of those of ordinary skill in the art.

Hemodialysis is often performed with a dialysate input volume flow rate of 500 cc/minute. The ultrafiltration rate normally falls wthin the range of 0–20 cc/minute. The ultrafiltration system of the present invention is capable, with a proper selection of components, of operating at the nominal rates of the prior art devices and any other desired dialysate flow rate. Also, there is no limit to the ultrafiltration rate attainable by the ultrafiltration system of the present invention except as limited by the rupture strength of the membrane 13. Thus, the system of the present invention provides ultrafiltration rate measurement and control not heretofore available in prior art systems. With a proper selection of components, it is possible to maintain the control of the ultrafiltration rate with any desired limits although, it is anticipated that an accuracy in the range of 1 cc/minute will be more than adequate.

Obviously, many modifications and alterations of the present invention will be apparent to those skilled in the art from the above description. For example, either the flow meter 31 or the receptacle 32 may be eliminated dependent upon the circumstances surrounding the hemodialysis. Also, depending on the transmembrane pressure gradient, the pressure attenuator 24 and pressure amplifier 25 may be either a pump or a valve. The ultrafiltration system of the present invention may be utilized within a common dialyzer-dialysate circuit, as illustrated, or, alternatively, may be employed within a separate ultrafiltration circuit. It is therefore to be understood that the invention may be practiced otherwise than is specifically decribed within the scope of the appended claims.

We claim:

1. In a hemodialysis system, an improved ultrafiltration circuit which comprises:
   input pump means;
   pressure attenuator means interconnecting said input pump means and the dialyzer dialysate input;
   output pump means;
   pressure amplifier means interconnecting said output pump means and the dialyzer dialysate output, said pressure attenuator means and said pressure amplifier means cooperating to control dialyzer pressure on the dialysate side;
   means for maintaining the volume flow of said input and output pump means substantially equal; and
   means for accepting any dialysate from the dialyzer output which exceeds the volume flow of said output pump means.

2. The ultrafiltration circuit of claim 1 wherein said dialysate accepting means comprises means for providing an instantaneous ultrafiltration rate.

3. The ultrafiltration circuit of claim 1 wherein said dialysate accepting means comprises means for providing a measurement of total ultrafiltration volume.

4. The ultrafiltration circuit of claim 1 wherein said dialysate accepting means comprises first means for providing an instantaneous ultrafiltration rate and second means for providing a measurement of total ultrafiltration volume.

5. The ultrafiltration circuit of claim 1 wherein said pressure attenuator means and said pressure amplifier means comprise pump means.

6. The ultrafiltration circuit of claim 1 wherein at least one of said pressure attenuator means and said pressure amplifier means comprises pump means.

7. The ultrafiltration circuit of claim 6 wherein said dialysate accepting means comprises means for measuring the ultrafiltration rate.

8. An ultrafiltration control and measurement system for a hemodialysis system which includes a dialyzer having blood flow ports and dialysate input and output ports, comprising:
- a first pressure control means connected to the dialysate input port of said dialyzer;
- a second pressure control means connected to the dialysate output port of said dialyzer, said first and second pressure control means cooperating to establish and control the dialysate pressure in said dialyzer so as to establish ultrafiltration therein;
- conduit means connected from the output of said second pressure control means to the input of said first pressure control means, said conduit means providing a fluid path in which dialysate recirculation may take place;
- a receptacle connected in said conduit means in fluid communication therewith;
- dialysate input pump means for pumping dialysate with the ouput of said pump connected to the portion of said conduit between said receptacle and said first pressure control means for supplying dialysate thereto; and
- dialysate exhaust pump means connected to the portion of said conduit between said second pressure control means and said receptacle for withdrawing fluid from the conduit at a flow rate substantially equal to the dialysate supply flow rate provided by said dialysate input pump means, whereby a volume of fluid flow equal to the ultrafiltration rate is diverted to said receptacle.

9. Apparatus according to claim 8 wherein said first pressure control means comprises a pressure attenuator, and said second pressure control means comprises a pressure amplifier.

10. Apparatus according to claim 8 wherein said first pressure control means comprises a valve and said second pressure control means comprises a pump.

11. Apparatus according to claim 10 further including control devices connected to said valve and to said pump which comprises said second pressure control means, said control devices operable for controlling the pressure in the dialysate side of said dialyzer.

12. Apparatus according to claim 8 wherein said first and second pressure control means each comprises a pump.

13. Apparatus according to claim 12 further including control devices connected to said pumps which comprise the first and second pressure control means, said control device operable for adjusting the pressure on the dialysate side of said dialyzer.

14. Apparatus according to claim 8 further including flow meter means connected in fluid communication with said conduit means and said receptacle for providing an instantaneous ultrafiltration rate measurement.

15. Apparatus according to claim 8 wherein said receptacle includes means for providing a measurement of the total ultrafiltration volume.

16. Apparatus according to claim 8 further including pump control means connected to said dialysate input pump means and said dialysate exhaust pump means, for controlling the pumping rate thereof.

17. In a hemodialysis system, an improved ultrafiltration circuit which comprises:
- input pump means;
- first pressure control means interconnecting said input pump means and the dialyzer dialysate input;
- output pump means;
- second pressure control means interconnecting said output pump means and the dialyzer dialysate output, said first and second pressure control means cooperating to control dialyzer pressure on the dialysate side;
- means for maintaining the volume flow of said input and output pump means substantially equal; and
- means for accepting any dialysate from the dialyzer output which exceeds the volume flow of said output pump means.

* * * * *

UNITED STATES PATENT AND TRADEMARK OFFICE
CERTIFICATE OF CORRECTION

PATENT NO. : 4,021,341
DATED : May 3, 1977
INVENTOR(S) : Louis C. Cosentino and B. Steven Springrose It is certified that error appears in the above-identified patent and that said Letters Patent are hereby corrected as shown below:

Title - delete "HERMODIALYSIS" and insert
--HEMODIALYSIS--.

Column 1, line 5 - delete "te" and insert --the--

Column 3, line 32 - delete "te" and insert --the--

Signed and Sealed this nineteenth Day of July 1977

[SEAL]

Attest:

RUTH C. MASON
*Attesting Officer*

C. MARSHALL DANN
*Commissioner of Patents and Trademarks*